United States Patent [19]

Levitt et al.

[11] Patent Number: 4,975,458
[45] Date of Patent: Dec. 4, 1990

[54] 2-ALKYL-3-BENZOYLBENZOFURANS USEFUL FOR TREATING CARDIAC ARRHYTHMIA

[75] Inventors: Barrie Levitt, Mamaroneck, N.Y.; Morris Stolar; Ron Breiman, both of Tel Aviv, Israel

[73] Assignees: Taro Pharmaceuticals Industries, Ltd.; Taro Vit Industries, Ltd., both of Haifa Bay, Israel

[21] Appl. No.: 322,369

[22] Filed: Mar. 13, 1989

[51] Int. Cl.$^5$ .................... A61K 31/34; C07D 307/78
[52] U.S. Cl. ..................................... 514/469; 549/468
[58] Field of Search .................... 514/469; 549/468

[56] References Cited

U.S. PATENT DOCUMENTS 4,001,426  1/1977  Brenner et al. ............... 514/469
4,485,112  11/1984 Pestellini et al. .............. 514/469

OTHER PUBLICATIONS

*Chemical Abstracts*, vol. 81, 1974, 37442u.

*Primary Examiner*—Frederick E. Waddell
*Attorney, Agent, or Firm*—Levonna Herzog

[57] ABSTRACT

New 2-alkyl-3-(4-hydroxy-3,5-di-tert-butylbenzoyl)-benzofurans useful for treating cardiac arrhythmia, as well as pharmaceutical compositions containing these benzofurans and the method of treating cardiac arrhythmia therewith are disclosed.

8 Claims, No Drawings

2-ALKYL-3-BENZOYLBENZOFURANS USEFUL FOR TREATING CARDIAC ARRHYTHMIA

BACKGROUND OF INVENTION

This invention pertains to new alkylbenzoylbenzofurans and more particularly to new 2-alkyl-3-(4-hydroxy-3,5-di-tert-butylbenzoyl)benzofurans useful for treating cardiac arrhythmia, as well as pharmaceutical compositions containing these benzofurans and the method of treating cardiac arrhythmia therewith.

Cardiac arrhythmia is an important cause of death following myocardial infarction or from other cardiac pathology. Heretofore, drugs used to control this disorder such as quinidine, lidocaine and procainamide have manifested significant drawbacks. According to Goodman and Gilman, The Pharmacologic Basis of Therapeutics, 7th edition, pp.761-770, "About one third of the patients who receive quinidine will have immediate adverse effects that necessitate discontinuation of therapy . . . . Procainamide is useful for the treatment of a variety of arrhythmias, and it can be administered by several routes. Unfortunately its potency and versatility are marred by its short duration of action and high incidence of adverse reactions when it is used chronically . . . . Lidocaine has a narrow antiarrhythmic spectrum . . . . The main adverse effects are on the central nervous system . . . . Higher concentrations may cause decreased hearing disorientation, muscle twitich, convulsions or respiratory arrest."

The great need for improved antiarrhythmics is evident.

According to Gubin et al., Eur. J. Med. Chem.-Chim. Ther.(1974) 9, 19-25, 2-alkyl-3-(4-hydroxy-3,5-dialkylbenzoyl)benzofurans, wherein the 3,5-dialkyl groups each contain 1-3 carbon atoms, are useful intermediates for the preparation of antianginal agents, comprised of the corresponding 2-alkyl(aminoalkyloxy-3,5-dialkylbenzoyl)benzofurans. As is well known in the art, angina results from a narrowing of the coronary blood vessels, usually due to accumulation of plaque, whereas arrhythmia, i.e. irregular heart beat, is a result of a problem with the natural pacemaker. No cardiac activity of any kind has been attributed to 2-alkyl-3-(4-hydroxy-3,5-dialkylbenzoyl)benzofurans by Gubin et al.

SUMMARY OF THE INVENTION

An object of this invention is the provision of new compounds which have improved antiarrhythmic activity.

A particular object of this invention is the provision of new 2-alkyl-3-benzoylbenzofurans which have improved antiarrhythmic activity.

A further object of this invention is the provision of new pharmaceutical compositions useful for treating arrhythmia.

Another object of this invention is the provision of a new and improved method for treating arrhythmia.

These objects and others, which will become evident from the description below, are accomplished by our discovery of new 2-alkyl-3-benzoylbenzofurans of the following formula (I)

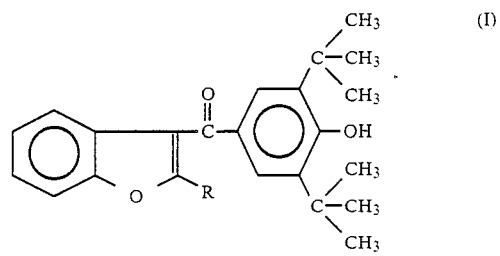

wherein R is an alkyl group containing 2 to 4 carbon atoms, and pharmaceutically acceptable salts thereof.

We have found that compounds of formula (I) display highly significant antiarrhythmic activity and thus provide an improved method for the treatment of arrhythmia.

DESCRIPTION OF THE INVENTION

Compounds of formula (I) wherein R is $C_2H_5$, n-$C_3H_7$, and n-$C_4H_9$ are preferred.

The preparation of compounds of formula (I) of the invention can be accomplished according to either of the following series of reactions, A or B.

Series A:

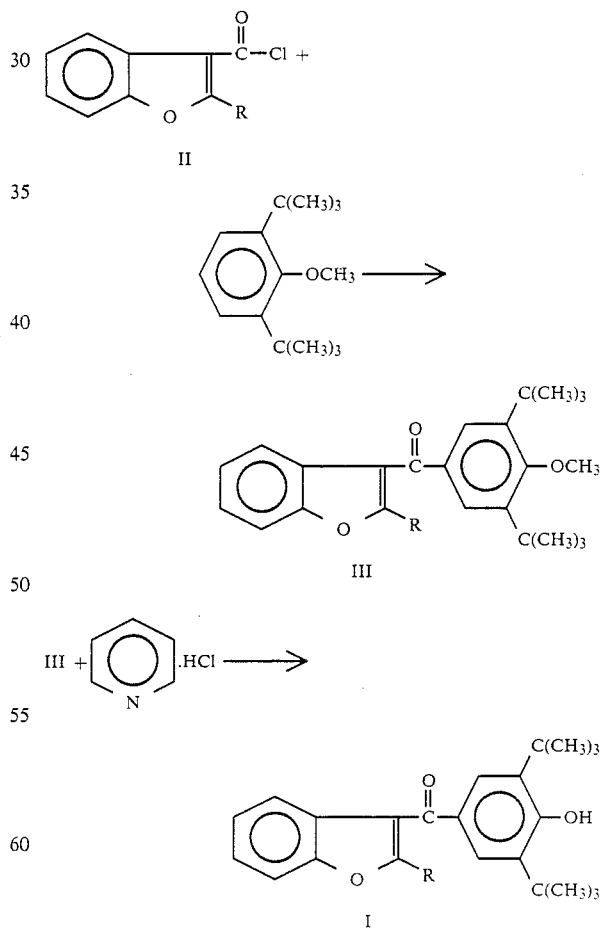

According to the A series of reactions, compounds of the invention (I) are prepared by Friedel-Crafts acylation of 2,6-di-tert-butylanisole with benzofurancarboxylic acid chlorides (II). The resulting methyl ether intermediate (III) is cleaved to the corresponding phenol (I) with pyridine hydrochloride.

Alternately, the compounds of the invention are prepared from a 2-alkylbenzofuran and 4-hydroxy-3,5-di-tert-butylbenzoyl chloride by Friedel-Crafts type, SnCl₄ catalyzed condensation, as shown in series B equations.

Series B:

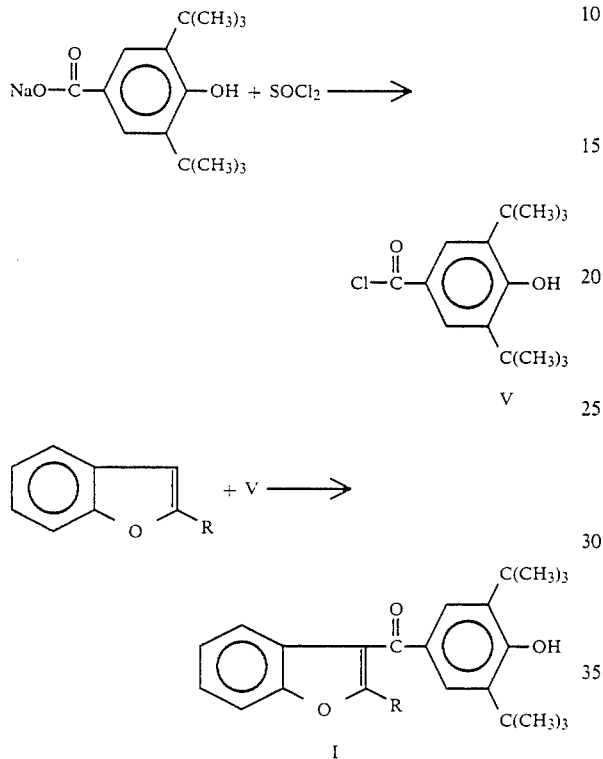

Compounds of the invention have improved antiarrhythmic activity. For example, 2-ethyl-3-(4-hydroxy-3,5-di-tert-butylbenzoyl)benzofuran, the compound of formula (I) wherein R=C₂H₅, when compared with lidocaine in a rat coronary ligation model, displayed superior activity in suppressing ventricular tachycardia, and was also superior in promoting survival of challenged animals. Thus, compounds of formula (I) can provide an improved level of antiarrhythmic activity together with diminished side effects.

The antiarrhythmic compounds of formula (I) can be formulated for use by the oral or parenteral routes. Acute emergency treatment would normally employ an intravenous form containing as an active agent, a pharmaceutically acceptable salt such as a sodium, potassium or calcium salt, etc. in an aqueous vehicle compatible with body fluids. The sterile, isotonic solution for such use is comprised of the soluble salt of the active drug in pyrogen-free water in the pH range of 10-11.5. Preservatives, such as benzyl alcohol, may be used, particularly in multiple dose formulations, to maintain sterility. Typical intravenous preparations may contain from 10-100 mg. of active compound, calculated as base, per ml. of solution. Administration of 0.5-10 mg. of active compound per kg. of patient body weight by the I.V. route every 6-8 hours is continued until a satisfactory cardiac rhythm is established.

Chronic therapy is customarily maintained by means of oral tablets or capsules containing 10-200 mg. of a compound of formula (I) per dose. As is usual in this art, the active compound is admixed with excipients such as lactose, starch, "Avicel" or the like, together with lubricants and dispersants such as stearic acid, magnesium stearate, silica, etc. in amounts necessary to confer appropriate disintegration and dissolution properties to the dosage form.

The usual antiarrhythmic maintenance dose will be in the range of 1-100 mg. of active compound per kg. of patient body weight daily, delivered in 3 to 4 divided doses or in a single sustained-release dose.

The following examples further illustrate the invention but must not be construed to limit the invention in any manner.

EXAMPLE 1

Synthesis of 2-ethyl-3-(4-hydroxy-3,5-di-tert-butylbenzoyl)benzofuran 3,5-Di-tert-butyl-4-hydroxybenzoic acid in an amount of 50 g. (0.2 mol) is dissolved in 250 ml. of warm methanol and mixed thoroughly for 30 minutes with an aqueous solution of 8 g. (0.2 mol) of NaOH in 40 ml. of water. The mixture is evaporated to dryness and the residual sodium salt is pulverized and dried. Petroleum ether in an amount of 300 ml. is added, the mixture is stirred and cooled to 5° C. and 100 ml. of thionyl chloride is added. After refluxing for 3 hours, 200 ml of dichloroethane is added and the mixture is distilled to remove unreacted thionyl chloride. The addition of dichloroethane and distillation of excess thionyl chloride is repeated two more times, and then the solution is cooled to room temperature. 2-Ethyl-benzofuran in an amount of 29.2 g. (0.2 mol) dissolved in 100 ml. of dichloroethane is added, and while stirring, 0.4 mol of anhydrous stannic chloride is added dropwise with cooling. The reaction mixture is then stirred overnight at room temperature. After cooling of 0° C., 1000 ml. of water is carefully added, the mixture is stirred for 1 hour and separated. The aqueous phase is extracted three times with 100 ml. of dichloroethane, and the combined organic phase is dried over Na₂SO₄, filtered and evaporated to dryness. The residual brown oil is recrystallized from petroleum ether to give 28 g. of white crystals having a melting point of 95°-100° C., which corresponds to a yield of 37%.

EXAMPLE 2

Synthesis of 2-n-butyl-3-(4-hydroxy-3,5-di-tert-butylbenzoyl)benzofuran

Following the procedure of Example 1, except for the substitution of 2-n-butylbenzofuran for 2-ethylbenzofuran, 2-n-butyl-3-(4-hydroxy-3,5-di-tert-butylbenzoyl)benzofuran, which has a melting point of 118°-120° C., is prepared with a yield of 38%.

EXAMPLE 3

Formulation of 10 mg./ml. I.V. Solution

An I.V. solution containing 10 mg./ml. of a compound of the invention is prepared with the following ingredients:

| | |
|---|---|
| Sodium salt of 2-n-butyl-3-(4-hydroxy-3,5-di-tert-butylbenzoyl)benzofuran, | 1.0 g. |
| Sodium chloride, | 0.9 g. |

| | |
|---|---|
| sodium hydroxide or citric acid in an amount to provide a pH of 8-10 and | |
| Sterile pyrogen-free water sufficient to make | 100 ml. |

To prepare the I.V. solution, 2-n-butyl-3-(4-hydroxy-3,5-di-tert-butylbenzoyl)benzofuran is dispersed in pyrogen-free distilled water and a 50% sterile sodium hydroxide solution is added to the dispersion until the benzofuran is dissolved. The pH of the solution is adjusted to 8-10 by the addition of sodium hydroxide or citric acid, followed by the addition of sufficient sodium chloride to provide isotonicity and sufficient pyrogen-free distilled water to make 100 ml. After thorough mixing, the solution is filtered through a sterile Millipore (0.4 μc) into a sterile container and then placed in ampules and/or vials.

EXAMPLE 4

Formulation of 100 mg./ml. I.V. Solution

An I.V. solution containing 100 mg./ml. of a compound of the invention is prepared with the following ingredients by the procedure set forth in Example 3:

| | |
|---|---|
| Potassium salt of 2-n-butyl-3-(4-hydroxy-3,5-di-tert-butylbenzoyl)benzofuran | 10.0 g. |
| Sodium chloride | 0.8 g. |
| Sodium hydroxide or citric acid sufficient for a pH of 8-10, and s | |
| Sterile pyrogen-free water to make | 100 ml. |

EXAMPLE 5

Formulation of 50 mg. Tablets

Tablets containing 50 mg./tablet of 2-n-butyl-3-(4-hydroxy-3,5-di-tert-butylbenzoyl)benzofuran are prepared with the following ingredients:

| | Grams per 1000 Tablets |
|---|---|
| 2-n-Butyl-3-(4-hydroxy-3,5-di-tert-butylbenzoyl)benzofuran | 50.00 |
| Lactose D.C. | 200.00 |
| Cornstarch | 50.00 |
| Magnesium stearate | 1.50 |
| TOTAL WEIGHT | 301.50 |
| WEIGHT/TABLET | 0.3015 g. |

To prepare the tablets, 3-(4-hydroxy-3,5-di-tert-butylbenzoyl)benzofuran is blended with lactose and milled through Fitzmill Hammers forward, medium speed, equipped with a size 2B stainless steel screen. The milled powder is transferred to a V blender, followed by the addition of prescreened starch and magnesium stearate. The resultant mixture is blended for twenty minutes and then is transferred to the tabletting device and pressed into 10.3 mm. flat faced tablets weighing 301.5 mg. per tablet.

What we desire to claim and protect by Letters Patent is:

1. A 2-alkyl-3-benzoylbenzofuran of the formula

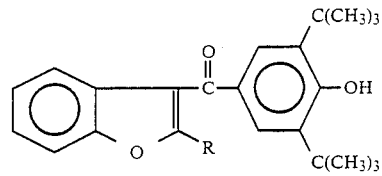

wherein R is an alkyl group containing 2 to 4 carbon atoms, and pharmaceutically acceptable salts thereof.

2. The 2-alkyl-3-benzoylbenzofuran according to claim 1, in which R is an ethyl, n-propyl or n-butyl group.

3. The 2-alkyl-3-benzoylbenzofuran according to claim 1, in which R is an ethyl group.

4. A pharmaceutical composition useful for treating cardiac arrhythmia comprising a compound according to claim 1 in a therapeutically effective amount in combination with a pharmaceutically acceptable carrier.

5. A pharmaceutical composition useful for treating cardiac arrhythmia comprising a compound according to claim 3 in a therapeutically effective amount in combination with a pharmaceutically acceptable carrier.

6. A pharmaceutical composition useful for treating cardiac arrhythmia in the form of an oral tablet comprising a compound according to claim 1 in a therapeutically effective amount in combination with a pharmaceutically acceptable carrier.

7. A method of treating a patient suffering from cardiac arrhythmia which comprises administering to said patient a therapeutically effective amount of a 2-alkyl-3-benzoylbenzofuran of the formula

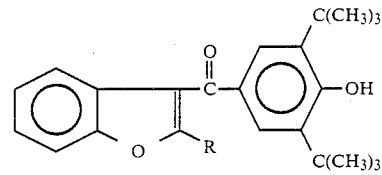

wherein R is an alkyl group containing 2 to 4 carbon atoms, or a pharmaceutically acceptable salt thereof.

8. The method of treating a patient suffering from cardiac arrhythmia according to claim 7 in which a therapeutically effective amount of the 2-alkyl-3-benzoylbenzofuran is administered, wherein R is an ethyl group.

* * * * *